United States Patent [19]

Doevenspeck

[11] Patent Number: 4,994,160
[45] Date of Patent: Feb. 19, 1991

[54] ELECTRIC-IMPULSE METHOD FOR TREATING SUBSTANCES AND DEVICE FOR CARRYING OUT THE METHOD

[76] Inventor: Heinz Doevenspeck, Sigurdstr. 1, D-4950 Minden, Fed. Rep. of Germany

[21] Appl. No.: 677,040

[22] Filed: Nov. 30, 1984

[30] Foreign Application Priority Data

Dec. 9, 1983 [DE] Fed. Rep. of Germany ....... 3344668
Apr. 11, 1984 [DE] Fed. Rep. of Germany ....... 3413583

[51] Int. Cl.⁵ .............................................. H05F 3/00
[52] U.S. Cl. ..................................... 204/165; 422/22; 210/748
[58] Field of Search .......................... 204/165; 422/22; 210/748

[56] References Cited

U.S. PATENT DOCUMENTS 4,139,439 2/1979 Manuccia et al. .................. 204/165

FOREIGN PATENT DOCUMENTS 0861332 9/1981 U.S.S.R. ............................. 210/748
0948784 2/1964 United Kingdom ................. 422/22

Primary Examiner—John F. Niebling
Assistant Examiner—Steven P. Marquis
Attorney, Agent, or Firm—Burns, Doane Swecker & Mathis

[57] ABSTRACT

In the electric-impulse method, substances to be treated are subjected successively in time to impulse groups of electro-magnetic fields having varying energy densities, in order to increase the yield of the reactions initiated. The electric impulses or impulse groups are generated by discharging charged capacitors, which have a varying capacitance (C1,C2,C3), along a discharge path (A1,A2), the discharge paths being formed by electrodes (11,12,13) between which the substances to be treated are located in an electrolyte.

12 Claims, 2 Drawing Sheets

ELECTRIC-IMPULSE METHOD FOR TREATING SUBSTANCES AND DEVICE FOR CARRYING OUT THE METHOD

DESCRIPTION

The invention relates to an electric-impulse method for treating substances in accordance with the pre-characterizing clause of Claim 1, and to a device for carrying out the method according to the precharacterizing clause of Claim 12.

Methods and devices of the generic type are known from German Patent No. 1,237,541. This patent describes the principles of the electric-impulse method which is suitable for treating organic and inorganic substances in a variety of ways. Special fields of application of the electric-impulse method are found in recovering individual phases from dispersed systems which is of considerable significance in breaking down comestibles, for example in recovering sugar, isolating the individual phases (protein, fat, water and so forth) of meat products and so forth. In this patent it has also already been found (column 8, lines 16–20) that this method can be used for destroying bacteria (microorganisms). This is of great significance in food preparation and the treatment of drinking and waste water. The electric-impulse method is thus a genuine alternative to the radiation treatment of comestibles in which radiation of very short wavelength is used. It is also known that chemical reactions can be triggered by electric impulses and that even molecular chains of organic and inorganic substances can be grown (gene manipulation, growing of molecular chains, for example for producing thin carbon filaments).

The fundamental nature of the electric-impulse method lies in exposing the substances present in an electrolyte or the substances which themselves form an electrolyte to short electric and/or electromagnetic fields in order to trigger the desired reactions. In this arrangement, these fields are generated by discharging one or several capacitors along a discharge path which is formed by at least two electrodes and in which the substances to be treated, in conjunction with the electrolyte, act as dielectric. The important factor is that the electric-impulses have steep rising edges. Depending on the reaction desired (breaking up disperse systems; destroying bacteria or growing substances), different energy levels are used ("hard", "medium soft" and "soft" pulses).

A circuit for generating such electric impulses is described in German Patent No. 1,233,958. The mains voltage is transformed up via a mains transformer and used for charging via a thyratron acting like a valve. For discharging, the capacitors can be connected via thyristors to the associated discharge paths. The important factor is that during the charging phase, the capacitors are isolated from the discharge paths whilst in the discharging phase, they are isolated from the power supply.

From German Patent No. 1,946,267 it is known to arrange discharge paths (electrodes) which are arranged behind each other in the direction of movement of the substances. In this arrangement, each discharge path (electrodes and dielectric) act as a capacitor.

German Offenlegungsschrift No. 2,907,887 discloses that with the electric-impulse method, especially when destroying bacteria (waste water purification) and desalinating solutions, some chemical reactions can be improved by dosed addition of oxidants or reductants. This has also been reflected in the essay by H. Hülsheger et al. ("Radiat Environ Biophys", 1981, 20:53–56) and in another essay by H. Hülsheger et al. ("Radiat Environ Biophys" 18, 281–288 (1980)). Investigation in these papers particularly covered the rate of destruction of bacteria as a function of additives, impulse amplitude and impulse duration as well as temperature and impulse frequency when using the impulse method.

The fundamental chemical and molecular relationships of the electric-impulse method are also described in an essay by Manfred Eigen "The "immeasurably" fast reactions" (reprint from Le Prix Nobel 1967, pages 151–180).

Similarly, J. Bernhardt, in his essay "Biological Effects of Electro-magnetic Fields" (journal Naturforschung 34c, 616–627 (1979)) deals with the electric-impulse method and describes the growing of cell chains (beaded chains) under the influence of an electric field. He points out, however, that pulsed fields are no more effective than continuous fields having the same mean field energy which has not been found to be correct by the present invention, since no residual ions (radicals) must be generated for a proper reaction to occur.

The influence of magnetic fields on chemical reactions is mentioned in the journal UMSCHAU 78 (1978), volume 2, page 54.

In the journal BIOELECTRO CHEMISTRY AND BIOENERGETICS 3, 58–83 (1976), the influence of external electric fields on cell membranes is described and a reference to short electric-impulses in a discharge chamber of a highvoltage circuit is again mentioned. The comment is also made that the resistance of the membrane is proportional to the thickness of the membrane for very short current impulses.

Finally, German Offenlegungsschrift No. 3,116,623 describes the influence of continuous circulation of the substances (by a "winding module") during the electric-impulse treatment.

However, all methods hitherto used or devices hitherto constructed are encumbered by the disadvantage that the desired reactions are not always initiated precisely enough so that the yield is not satisfactory for large-scale utilization.

The invention has the objective, therefore, of improving the generic method and the generic device in such a manner that a higher yield is obtained.

Thus the fundamental idea of the invention lies in using, during the treatment of the substances, varying energy densities in order to initiate selectively and deliberately certain reactions, particularly to destroy deliberately certain types of bacteria. Impulse groups of varying energy density are used, an impulse group containing an arbitrary number of individual impulses, including also the case in which an "impulse group" contains only a single impulse. If an impulse group contains several individual impulses, these individual impulses have the same energy density in each case.

The invention is based on the finding that varying energy densities are needed for destroying different bacteria. For example, the minimum energy density is a function of the size of the cell structure, the age of the cell or on whether the cell is gram-negative or gram-positive. For example, "young" cells still in their growth phase can be destroyed with lesser energy densities than "older" cells. The invention also takes into consideration that, in practice, it is difficult to determine several reaction parameters accurately which can even change during the treatment of the substances, which is attributable, among others, to the fact that preceding electric-impulses will change, for example, the dielectric constant of the substances. Thus, using several electric-impulses of varying energy density balances out these changes since the probability is increased that the electric-impulse having the "correct" energy density and initiating the desired reaction is also present. Although, theoretically, it would also be possible to work with relatively high energy densities, for example with field strengths of 20–25 kV/cm which would certainly exceed the required energy density for virtually all bacteria, this has the disadvantage, apart from excessive energy consumption, that single electric "breakdowns" would occur involving the formation of plasma and residual ionization and that the electrolyte would heat up severely. In many cases of application, this heating is undesirable since it falsifies the treatment result and since heated waste waters are not allowed to be discharged into the sewers or into rivers, for reasons of laws pertaining to the waterways.

Finally, in waste water processing it is not even desirable to destroy all bacteria since certain types of bacteria are desirable for later biological waste water processing and would have to be added again later.

Advantageous embodiments and developments of the invention can be found in the subclaims.

In the text which follows, the invention is explained in greater detail with the aid of illustrative embodiments and in connexion with the drawing, in which.

Figure 1:
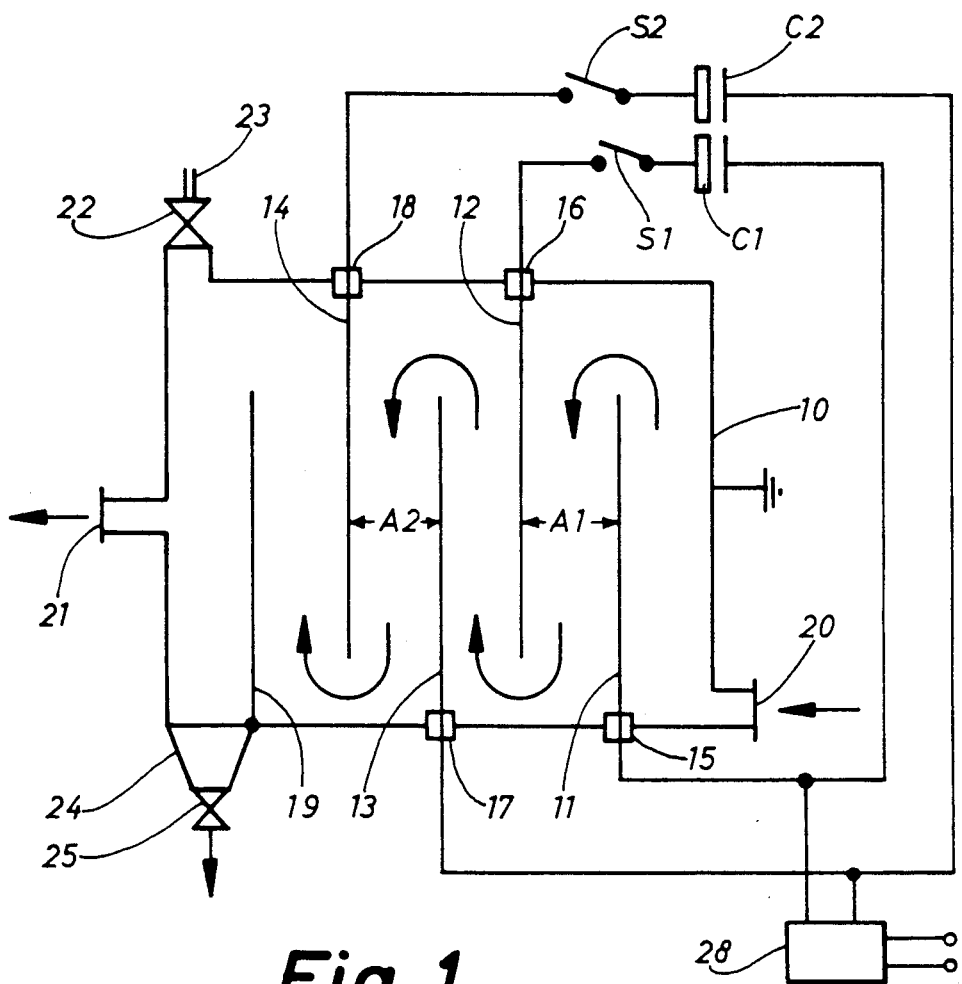
FIG. 1 shows a sketch of the principle of a device according to the invention for treating substances dissolved in liquid.

The device of FIG. 1 is particularly suitable for treating liquid substances or treating substances dissolved in liquid. A housing 10 has several walls 11, 12,13,14 which project inward from the inside wall of the housing and which are constructed as electrodes, for example steel or carbon electrodes. In addition, these walls project into the interior of the housing 10 in such a manner that in each case adjacent walls stand away from opposite sides of the housing. In this arrangement, the individual walls 11 . . . 14 project into the interior of the housing 10 only to such an extent that they do not reach the opposite wall. This arrangement creates a compulsory meandering path for the substances to be treated. The direction of movement is indicated by arrows. The walls 11 . . . 14 are electrically insulated with respect to the electrically conductive and earthed housing 10 which is performed by insulators 15,16,17 and 18. FIG. 1 shows another wall 19 which is electrically connected to the housing 10 and is thus earthed. This wall also forms a baffle or deflection plate for establishing the flow path. The housing 10 has an inlet 20 through which the substances to be treated can be supplied continuously or intermittently. From there they flow along the flow path described until, after passing the flow path, they reach an outlet 21 on the downstream side of the wall 19. This outlet 21 is located approximately halfway up the housing. Incidentally, the basic diagram of FIG. 1 is a side view, that is to say the liquid flows vertically upwards or vertically downwards between the respective plates. At the top of the housing 10 near the outlet 21, a venting valve 22 is provided which has an air outlet 23 to the atmosphere. Opposite to this, a sludge catcher 24 with outlet valve 25 is provided at the bottom of the housing 10 in the area of the outlet 21.

In the illustrative embodiment of FIG. 1, electrodes 11 and 12 and 13 and 14 each form a pair of electrodes and thus, between themselves, a discharge path A1 and A2, respectively. In this illustrative embodiment, the electrodes 11 and 12 can be electrically connected to a first capacitor C1 and the electrodes 13 and 14 can be electrically connected to a second capacitor C2. For this purpose, the electrodes 11 and 13 are each directly connected to a terminal of the associated capacitor C1 and C2, respectively, whilst the electrodes 12 and 14 are connected via electric switches S1 and S2, respectively, to the other terminal of the associated capacitor C1 and C2, respectively. The capacitors C1 and C2 can be charged up to predetermined voltage values via a charging and control device 28. If the switches S1 or S2 are closed, the capacitors C1 or C2 are discharged via the discharge paths A1 and A2, respectively. This generates an electric-impulse of high energy density. According to the invention, the capacitors C1 and C2 have different capacitance values so that they generate electric-impulses of different energy density when discharged. Since the substances to be treated successively first pass the discharge path A1 and then the discharge path A2, electric-impulses of varying energy density are applied to them during this progress which achieves the higher yield aimed for with the invention. In addition, provision can be made by the control unit 28 for the two capacitors C1 and C2 to be charged up to varying voltage amplitudes. It is also possible to design the spacings between the electrodes of the individual pairs of electrodes to be of varying magnitude which varies the capacitance value of the discharge paths. This is because, seen electrically, the discharge paths also form capacitors consisting of a pair of electrodes and the electrolytic substance flowing past between them and acting as dielectric.

Provision can be made for each particle of the substance to be exposed several times to groups of electric-impulses of the various energy densities as a function of the flow velocity of the substances to be treated and as a function of the switching frequency of the switches S1 and S2, respectively. Switching frequencies of up to 50 Hz are possible for the switches S1 and S2. In contrast, impulse times of longer than 20 ms have been found to be disadvantageous since then impulses are generated the peak value of which is maintained for a longer period. But this can give rise to residual ionizations which are undesirable.

Values in the order of magnitude of 2.5–20 $\mu$F have been found to be advantageous values for the capacitors C1 and C2, the capacitors being charged to voltages of between 8 and 12 kV. Thyristors or thyratrons are advantageously used as electric switches S1 and S2. As will still be explained below in connexion with FIG. 3, it is important that charging and discharging of the capacitors C1 and C2 take place separately in time since otherwise the charging voltage could be directly applied to the discharge path which would falsify the pulse duration and shape of the electric-impulses. This is why care must be taken that the switches S1 and S2, respectively are closed during the charging of the capacitors C1, C2 and conversely that the charging voltage from the control device 28 does not reach the capacitors during the discharging of the capacitors C1 and C2 (closed switches S1 and S2).

From the circuit of the capacitors C1 and C2 in FIG. 1, it can be seen that only two discharge paths A1 and A2 are provided in this circuit since the capacitors C1 and C2 are isolated from each other with respect to potential. If one terminal of each of the two capacitors is connected to a common potential, for example by electrically connecting the electrodes 11 and 13, the electrodes 12 and 14 form another pair of electrodes via which the capacitor C1 can be discharged.

The switches S1 and S2 can be operated in synchronism with each other but it is also possible to operate them alternately or completely asynchronously with respect to each other.

The capacitor discharge generates electro-magnetic fields of high energy density in the substances to be treated. Due to the fact that the capacitors C1 and C2 have different values, the energy densities of the individual discharge paths are also different. This can also be achieved by charging the capacitors C1 and C2 to different voltage amplitudes. For many applications it is useful first to apply impulses of low energy density and later impulses of high energy density to the substances to be treated. For such cases, the value of the capacitance of capacitor C1 is smaller (lower energy density) than that of the capacitor C2 (higher energy density). In the reverse case, which is also practicable in many cases of application, falling energy densities are then obtained during the passage of the substances.

Figure 2:
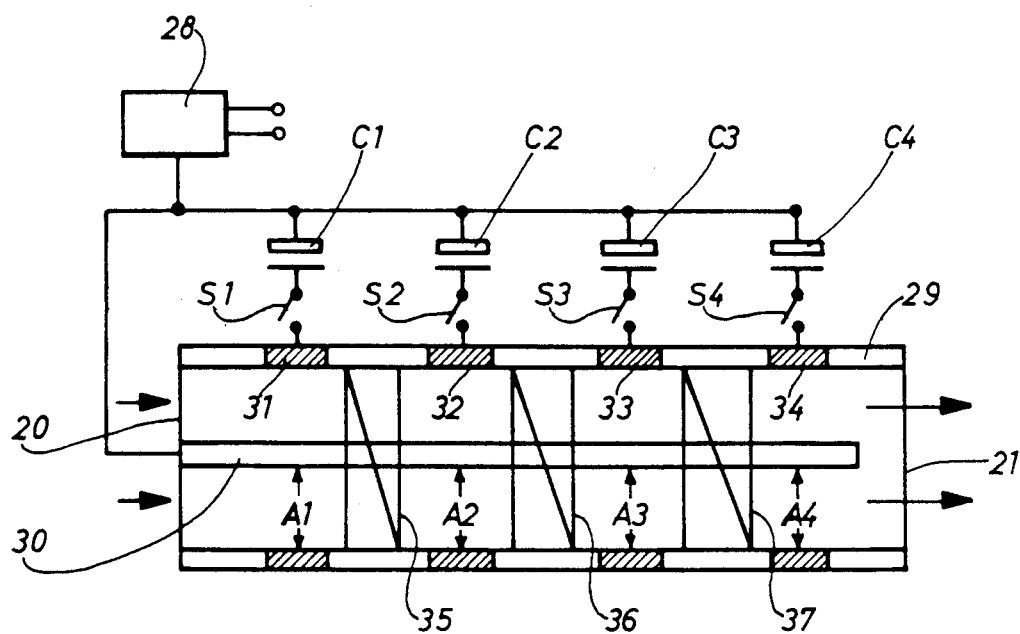
FIG. 2 shows a sketch of the principle of a device for treating paste-like substances and FIG. 3 shows a basic circuit diagram of an electric circuit used in the devices of FIGS. 1 and 2.

FIG. 2 shows diagramatically a side view of another illustrative embodiment which is particularly suitable for treating paste-like substances. For this, a housing 29 in the shape of a cylindrical tube or a polygonal elongated hollow body 29 is provided which has an inlet 20 and an outlet 21. In the center of the housing 29, a rod-shaped electrode 30 is arranged which is supported in any desired manner. In the walls of the housing peripheral electrodes 31 to 34 are arranged, adapted to the shape of the housing, which electrodes, for example in the case where the housing 29 is cylindrical, are annular electrodes. Between these electrodes and the common center electrode 30, four discharge paths are formed in this case. Capacitors C1 to C4 are again provided as impulse energy sources which can in each case be connected via switches S1 to S4 to an associated electrode 31 to 34. The center electrode 30 is connected to a common terminal of all capacitors C1 to C4. A control unit 28 again provides for the charging of the capacitors. The capacitors C1 to C4 have varying capacitance values also in this case. The paste-like substances are pressed through the housing 29 from inlet 20 to outlet 21 in the direction of the arrows so that, in the course of their passage, they pass through the individual discharge paths of the electrodes 31 to 34 where again impulses of varying energy densities are applied to them.

Since the polarity of the electric-impulses, related to the spatial alignment of the particles of the substance also plays a role in the treatment of the materials, it has been found that a higher yield can be achieved if the relative alignment between the electric fields and the particles is altered. For this, a variant of the invention provides for the spatial alignment of the particles to be changed while they are passing through the device. This can be achieved by guide plates 35,36, 37 which are arranged in the "field-free" space between adjacent electrodes and which provide for the particles to be agitated. Instead of the rigid guide plates 35,36, 37, a screw conveyor can also be provided which extends entirely or in sections through the housing 29.

According to another variant of the invention, the relative alignment between the field and the particles can be changed also by reversing the polarity of the individual capacitors, separately for each capacitor, or by charging successive capacitors in each case to a different polarity.

The electrode spacing can be changed also in the illustrative embodiment of FIG. 2. This provides a tapered or extending passage making it possible, especially in the former case, to create a screw press in combination with the screw conveyor mentioned. In this case, smaller holes can also be provided in the housing walls, through which holes liquid pressed out and/or released by the electric-impulses can drain away.

In the illustrative embodiment of FIG. 2, the switches S1 to S4 can be switched synchronously, asynchronously, in phase or in opposite phase.

Although the two illustrative embodiments of FIGS. 1 and 2 show several discharge paths A1 and A2, which are connected behind each other in the direction of movement of the substances to be treated, the invention can also be constructed with a single discharge path. For this, only one pair of electrodes is needed which can be connected via two or more switches to the same number of capacitors which have in each case different values of capacitance. By alternately operating the individual switches, electric-impulses of varying energy density can be applied to the only one discharge path.

Figure 3:
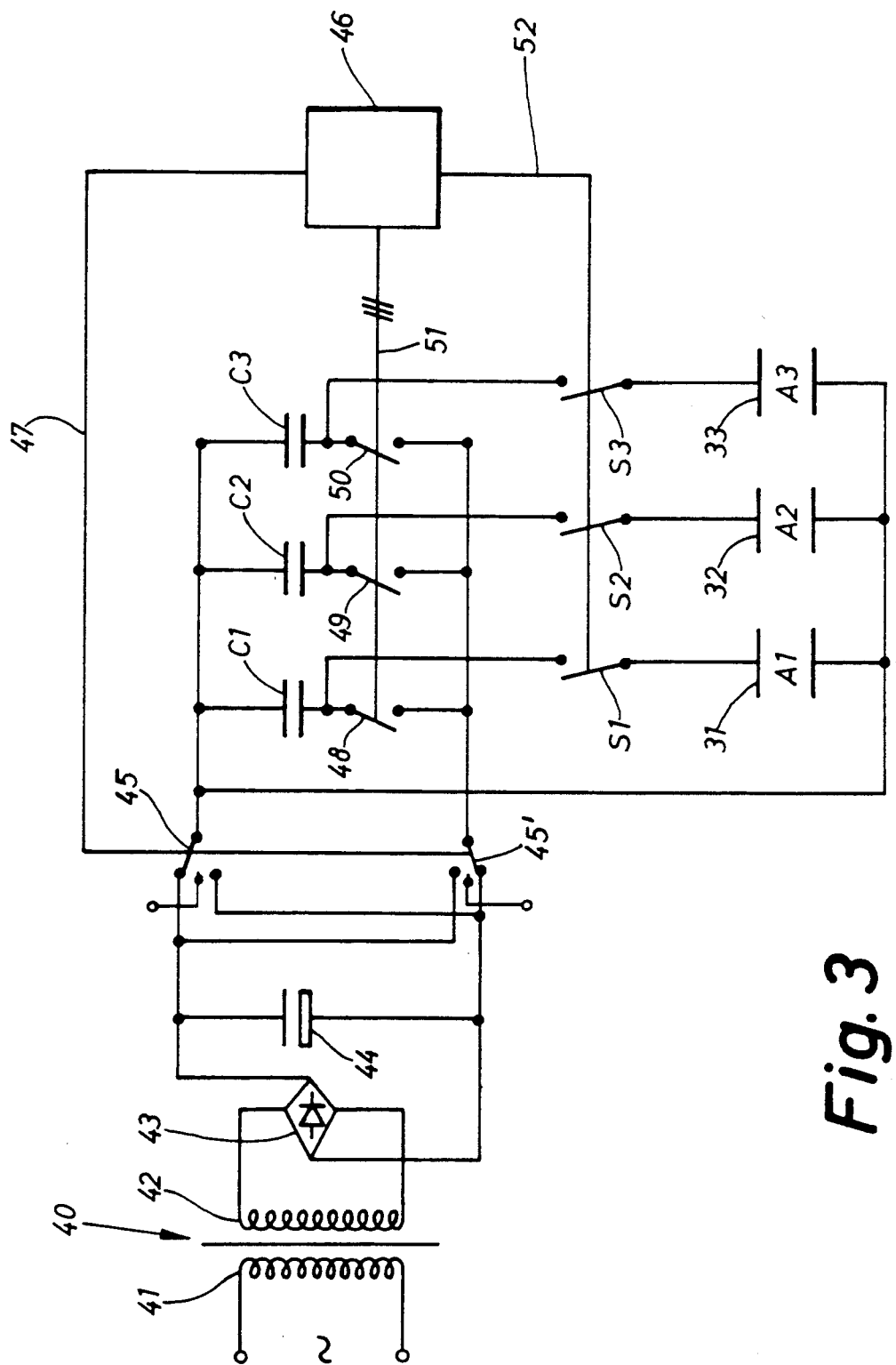

FIG. 3 shows a basic circuit diagram of a control and charging circuit for use in the device according to FIGS. 1 and 2. It is assumed that three capacitors C1, C2 and C3 having three discharge paths A1, A2 and A3, respectively, are provided. Correspondingly, there are three switches S1, S2, and S3. Mains voltage is transformed up to the required charging voltage of, for example, 8 kV via transformer 40 having the primary winding 41 and the secondary winding 42 and is then rectified in a bridge rectifier 43. The stepped up and rectified voltage is first smoothed and temporarily stored in a smoothing and buffer capacitor 44. The rectified high voltage is fed to the capacitors C1, C2 and C3 via pole changing switches 45 and 45', respectively. The pole changing switches 45 and 45', which can be operated by a control unit 46 via a control line 47, can be used to change the polarity of the charging voltage and a neutral intermediate position can be selected in which the capacitors C1 to C3 are completely isolated from the energy supply from the transformer 40. In an electric line from the switch 45' to one terminal each of the capacitors C1 to C3, switches 48,49 and 50 are here provided in each case which make it possible to charge only the capacitor which has a closed switch. This achieves that not all three capacitors C1 to C3 are simultaneously charged, thus limiting the load for the transformer 40 and hence for the mains. The switches 48 to 50 can in each case be separately operated by the control unit 46 via control lines 51.

The abovementioned switches S1 to S3, which can be opened or closed by the control unit 46 via a control line 52, are provided for discharging the capacitors.

As has already been described, care must be taken that the capacitors are charged and discharged separately in time. This is why the control unit 46 is constructed in such a manner that the switches S1 to S3 are at least open whenever the switches 45 and 45' are in one of their positions in which they supply rectified high voltage to the capacitors. Closing of the switches S1, S2 and S3 is thus possible only when the switches 45 and 45' are in their neutral position shown in which the energy supply is blocked off from the capacitors.

In the same manner, the control unit 46 provides for the switches 48,49 and 50 to be closed only when the switches 45 and 45' are also in one of their two end positions whilst, conversely, provision is made for the switches 48,49 and 50 to be opened whenever at least one of the switches S1 to S3 is closed.

It can be quite easily seen that the switches 48 to 50 can also be omitted. In this case, the three capacitors C1 to C3 are charged up in parallel.

An advantageous side effect of the device according to the invention consists in that it acts as a capacitive phase shifting device. In other words, the reactive current drawn by the device is predominantly capacitive. This is advantageous particularly because the reactive current presently drawn by electric motors and so forth from the mains is inductive and must be compensated by elaborate measures taken by the consumer or in the power station.

Electronic switches in the form of thyratrons or thyristors are used as switches also in the illustrative embodiment of FIG. 3.

Finally, the shape of the electric impulses generated shall be briefly discussed. These impulses have very steep rising edges (a few $\mu s$), they remain for a brief period (also $\mu s$) at their peak value with high-frequency oscillations and then decay in accordance with a function of e. The steepness of the decay of the function of e depends on the discharge time constant of the capacitors and of the associated discharge path. Discharging is not completely carried out in this arrangement. Rather, the associated switches S1 to S4 open after a predetermined time or as a function of a predetermined voltage value so that a residual voltage remains in the capacitors. The energy of the electric-impulses is proportional to the integral under the area of the impulses. The energy density (energy per time unit) is a function of the width of the impulses which, in turn, is determined by the discharge time constant and the peak of the impulses.

Naturally, the device according to the invention also makes it possible to vary in any manner the number of electric-impulses with the individual steps of energy density. For example, the substances can be exposed to a greater number of impulses in the region of the electrode 31 than at the remaining electrodes 32 to 34 of FIG. 2.

Supplementary to FIG. 2, it must be noted that the guide plates 35 to 37 can also be omitted. In this case, the center electrode 30 is supported by spacers which have to be constructed as insulators. It is also possible to design the electrode areas of the electrodes 31 to 34 to be of different sizes. Finally, it must also be pointed out that not all capacitors must have values which are different from those of the other capacitors. Thus, for example, the capacitors C1 and C3, on the one hand, and the capacitors C2 and C4, on the other hand, can have the same values of capacitance. As the substances pass through the device, they are then exposed twice in succession in each case to the same energy sequence.

Instead of a treatment space according to FIGS. 1 and 2, two or more separate devices of the type shown can also be connected behind each other. Individual devices of the type shown can also be connected in "bypass" in a treatment line. Although the housings and connecting lines of the individual devices are earthed, the electrolyte itself can still conduct considerable electric field strengths or electric energy densities from one housing to the other housings. In order to prevent this from happening, additional earthing means are provided in the area of the inlet and/or outlet of the individual housings, for example in the form of earthed screens or perforated plates so that the electrolyte flowing through these is essentially forced to earth potential.

If several devices are used for a treatment line, each device can operate with impulses of constant energy density so that the impulse groups of varying energy density occur at spatially separate positions. Naturally, it is also possible to generate, as described above, the impulse groups of varying energy density within each individual device.

All technical details shown in the claims, the description and the drawing can be essential to the invention both separately and in any desired combination with each other.

I claim:

1. Electric-impulse method for treating substances, particularly for obtaining individual phases from dispersed systems, for destroying bacteria or for growing molecular chains or organic and inorganic substances, in which the substances are exposed in an electrolyte several times successively in time to impulse-like electric and/or electro-magnetic fields wherein the energy density of the successive groups of electric impulses varies.

2. Electric-impulse method according to claim 1, characterized in that each group of electric impulses has between 1 and n individual electric impulses of the same energy density.

3. Electric-impulse method according to claim 1, characterized in that successive impulse groups have electric impulses of varying duration in time.

4. Electric-impulse method according to claim 1, characterized in that successive impulse groups have electric impulses of varying amplitude.

5. Electric-impulse method according to claim 1, characterized in that successive impulse groups have electric impulses having rising edges of varying steepness.

6. Electric-impulse method according to claim 5, characterized in that successive impulse groups have electric impulses of decreasing energy density.

7. Electric-impulse method according to claim 5, characterized in that successive impulse groups have electric impulses of decreasing energy density.

8. Electric-impulse method according to claim 5, characterized in that the time interval between successive electric impulses is greater than 20 ms.

9. Electric-impulse method according to claim 8, characterized in that the energy density of the electric impulses is selected in such a manner that no residual ionization occurs.

10. Electric-impulse method according to claim 9, characterized in that the voltage amplitude of the electric impulses is between 6 kV and 12 kV.

11. Electric-impulse method according to claim 10, characterized in that the electric impulses are generated by discharging capacitors having varying values of capacitance.

12. Electric-impulse method according to claim 11, characterized in that the electric impulses are generated by discharging capacitors which have been charged up to varying voltages.

* * * * *